(12) United States Patent
Kiper et al.

(10) Patent No.: US 7,964,720 B2
(45) Date of Patent: Jun. 21, 2011

(54) METHOD OF MAKING PORPHYRINS

(75) Inventors: Dilek Dogutan Kiper, Raleigh, NC (US); Marcin Ptaszek, Raleigh, NC (US); Jonathan S. Lindsey, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/960,057

(22) Filed: Dec. 3, 2010

(65) Prior Publication Data

US 2011/0105746 A1     May 5, 2011

Related U.S. Application Data

(62) Division of application No. 12/780,151, filed on May 14, 2010, which is a division of application No. 12/036,395, filed on Feb. 25, 2008, now Pat. No. 7,745,618.

(60) Provisional application No. 60/893,002, filed on Mar. 5, 2007.

(51) Int. Cl.
*C07D 487/22* (2006.01)
*C07B 47/00* (2006.01)

(52) U.S. Cl. ....................................................... 540/145

(58) Field of Classification Search ................... 540/145
See application file for complete search history.

(56) References Cited

U.S. PATENT DOCUMENTS

| | | | |
|---|---|---|---|
| 5,367,084 A | 11/1994 | Verkade et al. |
| 5,760,217 A | 6/1998 | Wijesekera et al. |
| 5,767,272 A | 6/1998 | Wijesekera et al. |
| 6,524,446 B2 | 2/2003 | Kulkarni et al. |
| 6,849,730 B2 | 2/2005 | Lindsey et al. |
| 6,916,982 B2 | 7/2005 | Loewe et al. |
| 6,924,375 B2 | 8/2005 | Lindsey et al. |
| 7,317,108 B2 | 1/2008 | Lindsey et al. |
| 7,323,561 B2 | 1/2008 | Lindsey et al. |
| 2005/0277770 A1 | 12/2005 | Balakumar et al. |
| 2006/0009638 A1 | 1/2006 | Lindsey et al. |
| 2006/0040914 A1 | 2/2006 | Roncucci et al. |
| 2006/0142562 A1 | 6/2006 | Lindsey et al. |
| 2007/0027311 A1 | 2/2007 | Lindsey et al. |
| 2007/0027312 A1 | 2/2007 | Lindsey et al. |
| 2007/0055060 A1 | 3/2007 | Lindsey et al. |
| 2007/0155963 A1 | 7/2007 | Lindsey et al. |

*Primary Examiner* — Paul V. Ward
(74) *Attorney, Agent, or Firm* — Myers Bigel Sibley & Sajovec, P.A.

(57) ABSTRACT

A method of making a compound of Formula I:

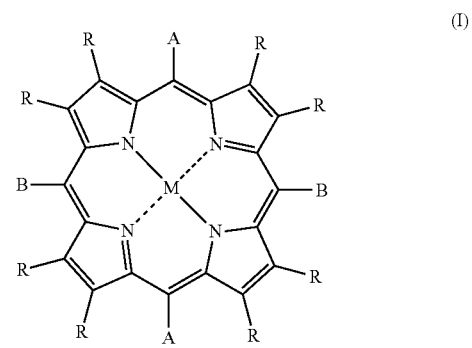

is carried out by condensing a pair of compounds of Formula II (which pair may be the same or different), or by condensing a compound of Formula III with a compound Formula IV,

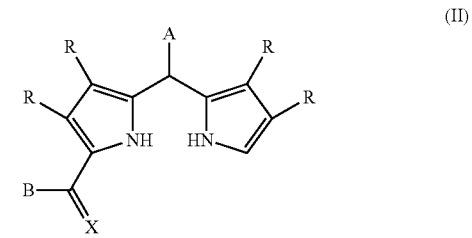

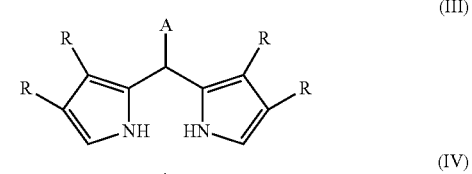

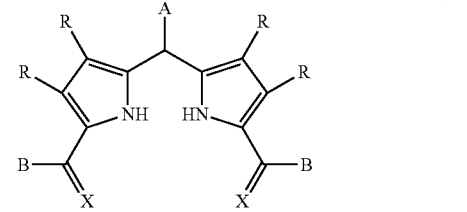

to produce a compound of Formula I. The condensing step may be carried out with a metal salt under basic conditions.

10 Claims, No Drawings

METHOD OF MAKING PORPHYRINS

RELATED APPLICATIONS

This application is a divisional of and claims priority to U.S. patent application Ser. No. 12/780,151, filed May 14, 2010, now allowed, which is a divisional of U.S. patent application Ser. No. 12/036,395, filed Feb. 25, 2008, now U.S. Pat. No. 7,745,618, and claims the benefit of U.S. Provisional Patent Application Ser. No. 60/893,002, filed Mar. 5, 2007, the disclosure of each of which is incorporated by reference herein in its entirety.

This application is related to Lindsey et al., Synthetic Route to ABCD-Porphyrins, Filed Feb. 12, 2007 (Appl. No. 60/889,344), the disclosure of which is incorporated by reference herein in its entirety.

This invention was made with Government Support under Grant Number GM36238 from the National Institutes of Health. The Government has certain rights to this invention.

FIELD OF THE INVENTION

The present invention concerns methods of making porphyrins, including both porphines and trans $A_2B_2$-porphyrins.

BACKGROUND OF THE INVENTION

Porphine (1, Chart 1) is the simplest porphyrin and represents the core macrocycle of naturally occurring and synthetic porphyrins. Accordingly, porphine has been the subject of various experimental and theoretical studies as a benchmark compound in porphyrin chemistry.[1] Due to the presence of 8 open β-pyrrole sites and 4 meso sites, porphine is a potential building block for the elaboration of porphyrin derivatives. In this regard, porphine undergoes selective mono-bromination at a β-position to give 2-bromoporphine, whereas the zinc chelate (Zn-1) undergoes reaction at a meso-position to give zinc(II) 5-bromoporphine.[3] On the other hand, Shi and Wheelhouse showed that the magnesium(II) chelate of porphine (Mg-1) undergoes tetrabromination to give magnesium(II) meso-tetrabromoporphine. Subsequent palladium-coupling reactions afforded the corresponding tetraaryl $A_4$-porphyrins, which included target porphyrins that are not easily available by other routes (e.g., with heterocyclic substituents).[2] Senge has shown that porphine reacts with organolithium reagents to provide meso-substituted A- or cis-$A_2$-porphyrins, which also are difficult to synthesize by other routes.[4] In addition, the iron complex of porphine was studied as a simple model of myoglobin.[5] These reports provide a glimmer of the possible synthetic utility of porphine; however, the practical use of porphine in synthetic chemistry and biochemistry has been thwarted by two vexing and somewhat interrelated limitations: (1) lack of an efficient method of synthesis of porphine, and (2) extremely low solubility of the free base porphine.

Chart 1

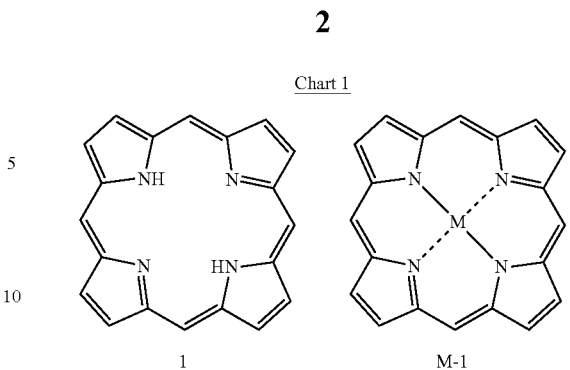

The reported methods for the synthesis of porphine over the past 70 years are summarized in Table 1. Fischer and Gleim obtained 17 mg of porphine by prolonged heating of 20 g of pyrrole-2-carboxaldehyde in formic acid.[6] In the same era, Rothemund obtained porphine from pyrrole and formaldehyde, albeit in very low yield (0.02%).[7] The yield was increased to 0.9% by slow addition of pyrrole and formaldehyde to propionic acid.[8]

A significant improvement was achieved by the use of 2-hydroxymethylpyrrole. Krol increased the yield of porphine up to 5% using 2-hydroxymethylpyrrole in glacial acetic acid containing a catalytic amount of magnesium acetate and potassium persulfate as an oxidizing reagent.[9] Other improvements were reported by Adler and Longo (addition of hydroxymethylpyrrole periodically over several days with ethylbenzene as solvent,)[10] and by Yalman (use of DMF as a solvent and metal salts afforded porphine in 20%,[11] although this yield has subsequently been claimed to be non-reproducible[12]). Recently, Ellis prepared porphine in a biphasic system in 15.3% yield.[12] The use of 1-hydroxypyrrole under micellar conditions afforded porphine in ~2% yield.[13]

In a related approach, N,N-dimethylaminomethylpyrrole has been utilized as a starting material. Copper(II)porphine was prepared from N,N-dimethylaminomethylpyrrole in two steps.[14] First, refluxing N,N-dimethylaminomethylpyrrole in chlorobenzene in the presence of ethylmagnesium bromide provided 2,3-dihydroporphine (chlorin) in 3.86% yield. The chlorin was quantitatively converted to copper(II)porphine by heating in acetic acid in the presence of copper(II) acetate. Formation of nickel(II)porphine was also observed as a byproduct in the synthesis of chlorin by simply heating N,N-dimethylaminomethylpyrrole in pyridine in the presence of nickel(II) acetate (yield was not reported).[15]

Currently, the most popular method for preparing porphine entails the dealkylation of tetrakis(tert-butylporphyrin) in the presence of strong acid.[16, 17] The tert-butyl groups can be located at meso- or β-positions. The yield of porphine upon dealkylation of meso-tetra(tert-butyl)porphine is 64-74%; however, this method requires the initial preparation of meso-tetra(tert-butyl)porphine. Porphine also can be prepared by the condensation of tripyrrin with 2,5-bis(hydroxymethyl)pyrrole and subsequent oxidation of the resulting porphyrinogen by p-chloranil in 31% yield.[18]

Despite the structural simplicity of porphine, there remains no method of satisfactory yield, scale, and ease of implementation that enables the synthetic capabilities of porphine to be unlocked. The major drawbacks of the existing routes are: (1) low yields of macrocycle formation, which can be compensated in some cases by the use of easily available starting materials (e.g., pyrrole and formaldehyde); (2) low concentration reactions; (3) long reaction times; (4) tedious separation of porphine from the large amount of polymeric material

3 in the crude reaction mixture; and/or (5) lengthy synthetic paths (e.g., five steps from commercially available starting material).

SUMMARY OF THE INVENTION

A first aspect of the invention is a method of making a compound of Formula I:

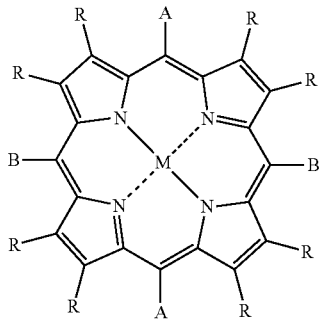

(I)

comprising: condensing (i) a pair of compounds of Formula II:

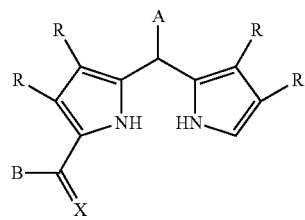

(II)

with (ii) a metal salt under basic conditions to produce said compound of Formula I.

A second aspect of the invention is a method of making a compound of Formula I:

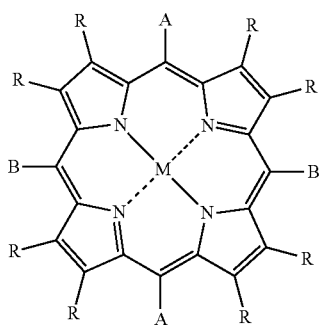

(I)

4 comprising condensing (i) a compound of Formula III with a compound Formula IV

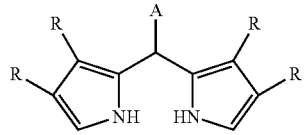

(III)

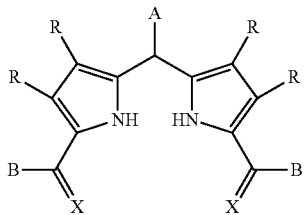

(IV)

with (ii) a metal salt under basic conditions to produce the compound of Formula I.

Groups "A", "B", "R", and "X" are as discussed in greater detail below.

The foregoing and other objects and aspects of the present invention are explained in greater detail in the specification set forth below.

DETAILED DESCRIPTION OF THE PREFERRED EMBODIMENTS

A. Definitions

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Hydroxyl" as used herein refers to an —OH group.

"Nitro" as used herein refers to an —$NO_2$ group.

"Alkyl" as used herein alone or as part of another group, refers to a straight or branched chain hydrocarbon containing from 1 or 2 to 10, 20 or 50 carbon atoms (e.g., C1 to C4 alkyl; C4 to C10 alkyl; C11 to C50 alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl, in some embodiments preferred, and refers to a straight or branched chain hydrocarbon group containing from 1 to 4 carbon atoms. Representative examples of loweralkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene" as used herein refers to a difunctional linear, branched or cyclic alkyl group, which may be substituted or unsubstituted, and where "alkyl" is as defined above.

"Alkenyl" as used herein alone or as part of another group, refers to a straight or branched chain hydrocarbon containing from 1 or 2 to 10, 20 or 50 carbon atoms (e.g., C1 to C4 alkenyl; C4 to C10 alkenyl; C11 to C50 alkenyl) (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadienyl, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkenylene" as used herein refers to a difunctional linear, branched or cyclic alkyl group, which may be substituted or unsubstituted, and where "alkenyl" is as defined above.

"Alkynyl" as used herein alone, or as part of another group, refers to a straight or branched chain hydrocarbon containing from 1 or 20 to 10, 20 or 50 carbon atoms (e.g., C1 to C4 alkynyl; C4 to C10 alkynyl; C11 to C50 alkynyl) (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Alkynylene" as used herein refers to a difunctional linear, branched or cyclic alkynyl group, which may be substituted or unsubstituted, and where "alkynyl" is as defined above.

"Alkylidene chain" as used herein refers to a difunctional linear, branched, and/or cyclic organic group, which may be substituted or unsubstituted, which may be saturated or unsaturated, and which may optionally contain one, two or three heteroatoms selected from the group consisting of N, O, and S. Examples include but are not limited to alkylene, alkenylene, alkynylene, arylene, alkarylene, and aralkylene. See, e.g., U.S. Pat. No. 6,946,533. The alkylidene chain may contain any suitable number of carbon atoms (e.g., a C1 to C4; C4 to C10; C10 to C20; C20 to C50).

"Alkoxy" as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxyacylamino, aminoacyloxy, linking groups, surface attachment groups, bioconjugatable groups, targeting groups, or a water soluble group.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Amide" as used herein alone or as part of another group refers to a —C(O)NR$_a$R$_b$ radical, where R$_a$ and R$_b$ are any suitable substituent such as H, alkyl, cycloalkyl, alkenyl, alkynyl or aryl.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Preferred heterocyclo groups include pyridyl and imidazolyl groups, these terms including the quaternized derivatives thereof, including but not limited to quaternary pyridyl and imidazolyl groups, examples of which include but are not limited to:

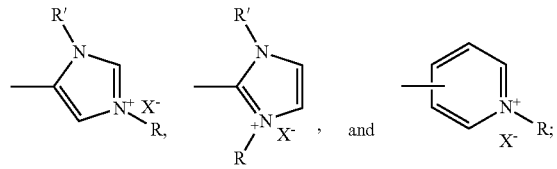

where R and R' are each a suitable substituent as described in connection with "alkyl" above, and particularly alkyl (such as methyl, ethyl or propyl), arylalkyl (such as benzyl), optionally substituted with hydroxy (—OH), phosphonic acid (—PO$_3$H$_2$) or sulfonic acid (—SO$_3$H), and X$^-$ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CHCHCH$_2$—, —CH$_2$CH$_2$CH$_2$CH$_2$CH$_2$CH$_2$—, etc. The term "spiroalkyl" is intended to include both substituted and unsubstituted "spiroalkyl" unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl S(O)$_m$, aryl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Aldehyde" as used herein refers to a group of the formula:

"Acetal" as used herein refers to a group of the formula:

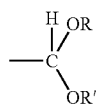

where R and R' are each suitable groups, e.g., groups independently selected from the group consisting of alkyl, aryl, alkylaryl, or where R and R' together form a group —R"— where R" is an alkylene (i.e., cycloalkyl). The acetal is preferably reasonably robust, and hence it is preferred that at least one, or more preferably both, of R and R' is not methyl, and it is particularly preferred that neither R nor R' is H.

"Macrocyclic ligand" as used herein means a macrocyclic molecule of repeating units of carbon atoms and hetero atoms (e.g., O, S, or NH), separated by the carbon atoms (generally by at least two or three carbon atoms). Macrocyclic ligands exhibit a conformation with a so-called hole capable of trapping ions or molecules, particularly cations, by coordination with the electrons of the hetero atom (e.g., a lone pair of electrons on the oxygen atoms when the hetero atoms are oxygen). In general, the macrocyclic ring contains at least 9, 12 or 14 carbon atoms and hetero atoms (e.g., O, S, NH), each hetero atom in the ring being separated from adjoining hetero atoms in the ring by two or more carbon atoms. The macrocyclic ring may be substituted or unsubstituted, and may be fused to additional rings (e.g., 1 to 4 additional rings such as phenylene, naphthylene, phenanthrylene, and anthrylene rings). The macrocyclic ligand may be in the form of a substituent. See, e.g., U.S. Pat. No. 6,411,164 to Sibert.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates)

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium as described above) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc. Note that compounds of the present invention can contain both an anionic group as one ionic substituent and a cationic group as another ionic substituent, with the compounds hence being zwitterionic. Note also that the compounds of the invention can contain more than one anionic or more than one cationic group.

"Protecting group" as used herein includes any suitable protecting group; "protected form" refers to a substituent in which an atom such as hydrogen has been removed and replaced with a corresponding protecting group. Protecting groups are known. See generally T. H. Greene and P. G. M. Wuts, *Protective Groups in Organic Synthesis,* 3rd edition, John Wiley & Sons, New York (1999). Examples include but are not limited to: hydroxy protecting groups (for producing the protected form of hydroxy); carboxy protecting groups (for producing the protected form of carboxylic acid); aminoprotecting groups (for producing the protected form of amino); sulfhydryl protecting groups (for producing the protected form of sulfhydryl); etc. Particular examples include but are not limited to: benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, acetyl (Ac or —C(O)CH$_3$), benzoyl (Bn or —C(O)C$_6$H$_5$), and trimethylsilyl (TMS or —Si(CH$_3$)$_3$), and the like; formyl, acetyl, benzoyl, pivaloyl, t-butylacetyl, phenylsulfonyl, benzyl, t-butyloxycarbonyl (Boc), and benzyloxycarbonyl (Cbz) and the like; and hemithioacetals such as 1-ethoxyethyl and methoxymethyl, thioesters, or thiocarbonates and the like. See, e.g., U.S. Pat. Nos. 6,953,782; 6,951,946; 6,951,942; and 6,051,724. Particularly preferred are halo, thio (e.g., alkylthio, thiocyanate), acetate, sulfonate, and triflate protecting groups.

"Antibody" as used herein refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

"Coupling agent" as used herein, refers to a reagent capable of coupling a photosensitizer to a targeting agent "Targeting agent" refers to a compound that homes in on or preferentially associates or binds to a particular tissue, receptor, infecting agent or other area of the body of the subject to be treated, such as a target tissue or target composition. Examples of a targeting agent include but are not limited to an antibody, a ligand, one member of a ligand-receptor binding pair, nucleic acids, proteins and peptides, and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (antiligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-alpha and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSF) and GMCSF receptor and macrophage colony stimulating factor (MCSF) and MCSF receptor.

"Linkers", or "linker groups" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

"Water soluble group" (or "water solubilizing group") as used herein generally includes substituents containing at least one ionic or polar group, coupled to the parent molecule directly or by means of an intervening linker. Examples include but are not limited to groups of the formula:

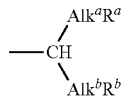

wherein $R^a$ and $R^b$ are each independently an ionic group or polar group, and $Alk^a$ and $Alk^b$ are each independently a C1-C50 alkylidene chain.

"Bronsted acid" as used herein refers to a molecular entity (and corresponding chemical species) that is a proton donor to a base. Any suitable Bronsted acid may be used as a catalyst, with examples including but not limited to: trifluoroacetic acid, trichloroacetic acid, oxalic acid, taurine, malonic acid, formic acid, acetic acid, and $NH_4Cl$.

"Lewis acid" as used herein refers to a molecular entity (and corresponding chemical species) that is an electron-pair acceptor and therefore able to react with a Lewis base to form a Lewis adduct, by sharing the electron pair furnished by the Lewis base. Any suitable Lewis acid may be used as a catalyst, examples including compounds of the general formula $LnX_3$ where Ln is a lanthanide and X is halo such as Cl, Br, I, etc., triflate or OTf, etc., and with examples specific examples including but not limited to: $Yb(OTf)_3$, $InCl_3$, $Sc(OTf)_3$, $MgBr_2$ and $CeCl_3$.

B. Methods of Making Porphine and Porphyrins Including trans $A_2B_2$-porphyrins As noted above, the present invention provides a method of making a compound of Formula I:

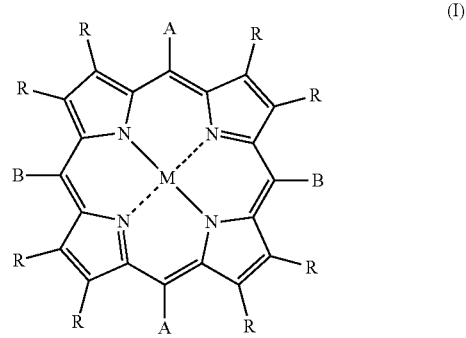

comprises condensing (i) a pair of compounds of Formula II:

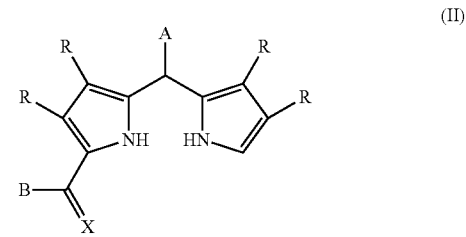

with (ii) a metal salt under basic conditions to produce said compound of Formula I.

In an alternate embodiment of the invention, a method of making a compound of Formula I as given above comprises condensing (i) a compound of Formula III with a compound Formula IV

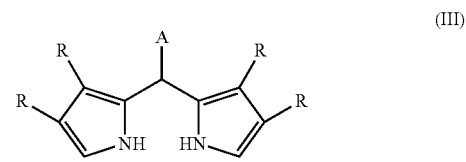

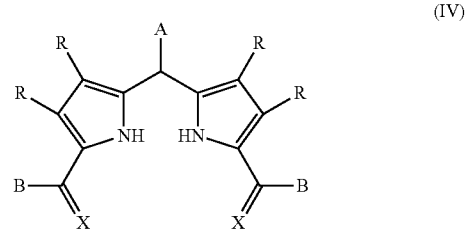

with (ii) a metal salt under basic conditions to produce the compound of Formula I.

In each of the foregoing reactions, X is selected from the group consisting of O, S, Se, NH, NR, $(OR)_2$, $(SR)_2$, and $(SeR)_2$, wherein R is as given below, preferably alkyl or aryl.

In each of the foregoing reactions, each A is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups.

In each of the foregoing reactions, each B is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, acyl, formyl, carboxylic acid, acylamino, alkylthio, amino, alkylamino, arylalkylamino, disubstituted amino, linking groups, surface attachment groups, bioconjugatable groups, targeting groups, and water soluble groups.

In each of the foregoing reactions, each R is independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, acetal, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups; or an adjacent pair of two R groups may together form an annulated arene or annulated alkene.

In some embodiments, the condensing step is preferably carried out in a non-coordinating solvent.

In some embodiments, the condensing step is preferably carried out in the presence of a non-nucleophilic base.

It will be appreciated from the foregoing that, when all groups "A", "B", and "R" are hydrogen, the present invention provides a convenient method of making porphine by (i) self-condensing 1-formyl dipyrromethane in the presence of a metal salt under such basic conditions to produce porphine, (ii) by condensing 1,9-diformyldipyrromethane with dipyrromethane under such basic conditions to produce porphine, or (iii) by concurrently both condensing 1-formyl dipyrromethane with itself while also condensing 1,9-diformyldipyrromethane with dipyrromethane under such basic conditions to produce porphine. Option (iii) above is advantageous when dipyrromethane is formylated to produce a mixture of dipyrromethane, 1-formyldipyrromethane, and 1,9-diformyldipyrromethane, as the mixture can then be used directly to make the metallated porphine.

Any suitable metal salt can be used, depending on the metal desired in the metalloporphyrin, with particular embodiments including but not limited to magnesium, zinc, nickel and indium salt. In some embodiments, magnesium halides are particularly preferred.

Reaction conditions are not in all embodiments critical. In some embodiments the reaction is carried out under basic conditions (e.g., with addition of a suitable base such as NaOH, ethylmagnesium bromide, 2-mesityl magnesium bromide, 2,2,6,6-tetramethylpiperidine, tetramethylguanidine, etc) added to the reaction mixture). The reaction may be solventless or may be carried out in a solvent. The solvent, if used, is typically an organic solvent (including mixtures), examples including ethanol, tetrahydrofuran (THF), valeronitrile, isovaleronitrile, butyronitrile, acetonitrile, xylene, mesitylene, chlorobenzene, dichlorobenzene, dichloromethane, chloroform, and toluene. The choice of specific solvent will depend upon the choice of metal salt, with some metals such as magnesium requiring a non-coordinating solvent such as toluene or chlorobenzene. In some preferred embodiments the reaction is carried out in a non-coordinating or weakly coordinating (but not strongly coordinating) solvent such as toluene, xylene, 1,2-dichlorobenzene, dichloroethane, chlorobenzene, anisole (or methoxybenzene), etc., including mixtures thereof, in the presence of a non-coordinating or mildly coordinating (but not strongly coordinating) base such as 1,8-diazabicyclo[5.4.0]-undec-7-ene (or "DBU"), DBN, 2,2,6,6-tetramethylpiperidine, 2,6-di-tert-butylpyridine, etc., including mixtures thereof.

The reaction is formally carried out in the presence of an oxidant, such as air (e.g., an open-atmosphere reaction without the inclusion of an additional chemical oxidant beyond ambient oxygen), although neither air nor a tradition exogenous oxident appears essential as discussed below. The reaction may be carried for any suitable time (e.g., from one hour to two days) and at any temperature, including room temperature and elevated temperatures (e.g., from room temperature or 25° C., up to 70, 100 or 200° C.), and/or with microwave irradiation, with any suitable concentration of reactants (e.g., 10 or 20 up to 500 or 1000 mM, with 100-200 mM currently preferred).

Once the porphyrin is formed, the metal can be displaced to form a free base thereof. Displacement of the metal can be carried out by any suitable technique, such as by displacement with an acid. See, e.g., 6,946,552 to Lindsey et al.

Choice of starting materials (Compounds of Formula II). When the two members of the pair of 1-acyldipyrromethanes of Formula II that undergo condensation are identical, the resulting porphyrin can be of the trans-$A_2B_2$ type wherein $A \neq B \neq H$. When $A \neq H$ and $B = H$, the resulting porphyrin is of the trans-$A_2$ type; alternatively, when $A = H$ and $B \neq H$, the resulting porphyrin again bears two substituents (derived from the B substituent) in a trans configuration. Again, such a porphyrin is referred to as a trans-$A_2$-porphyrin to indicate the presence of two meso substituents in a trans configuration.

When the two members of the pair of 1-acyldipyrromethanes that undergo condensation are not identical, the resulting reaction is statistical in nature and yields as many as three porphyrin products. For a first acyldipyrromethane bearing A/B substituents, and a second acyldipyrromethane bearing C/D substituents, the resulting porphyrins are the trans-$A_2B_2$-porphyrin, the trans-$C_2D_2$-porphyrin, and the ABCD-porphyrin. The latter porphyrin is the so-called "hybrid" product given that it is derived from the two dipyrromethanes. This statistical approach is attractive when one wants access to the hybrid porphyrin without carrying out the larger number of steps typical of a rational synthesis. However, the statistical mixture of porphyrins typically requires separation to obtain the target hybrid porphyrin.

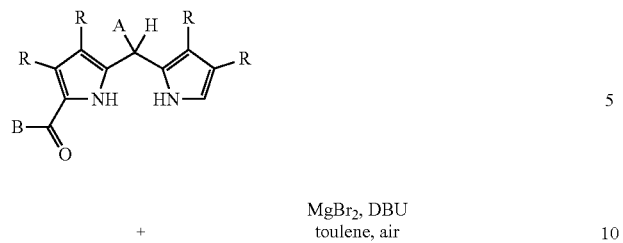
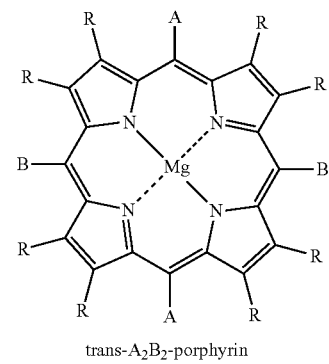

trans-$A_2B_2$-porphyrin

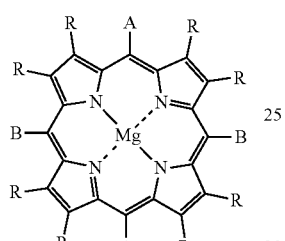

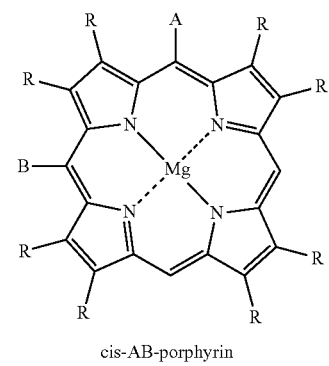

cis-AB-porphyrin

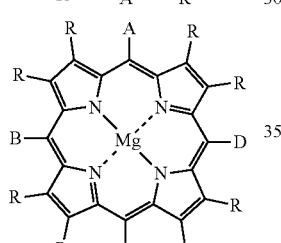

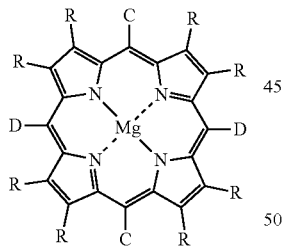

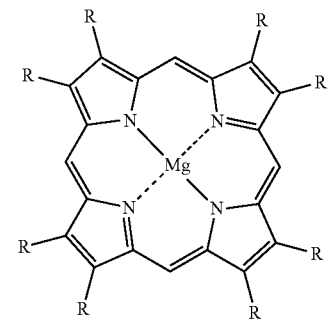

meso-unsubstituted porphyrin

Several non-limiting examples this hybrid approach are as follows:

(i) When C=D=H, and neither A nor B=H, the resulting porphyrins are the trans-$A_2B_2$-porphyrin (from self-condensation of the AB-substituted 1-acyldipyrromethane, the meso-unsubstituted porphyrin (derived from the CD-species, 1-formyldipyrromethane), and the hybrid porphyrin which contains a cis-AB substituent pattern. When C=D=H, and A=B, the hybrid porphyrin contains a cis-$A_2$ substituent pattern (not shown). When C=D=H, and one of A or B but not both=H, the resulting hybrid porphyrin contains a single substituent (A-porphyrin) (not shown). Such sparsely substituted porphyrins (cis-AB-, cis-$A_2$-, and A-porphyrins) are of interest for a number of applications as discussed in section C below yet are difficult to access via rational routes.

(ii) When C=D≠H, and neither A nor B=H, the resulting porphyrins are the trans-$A_2B_2$-porphyrin, the porphyrin with four identical substituents (derived from the $C_2$-substituted 1-acyldipyrromethane), and the hybrid porphyrin which contains a cis-$ABC_2$ substituent pattern. When A=B, the hybrid porphyrin contains a cis-$A_2C_2$ substituent pattern. Such cis-substituted porphyrins are of interest for a number of applications as discussed in section C below.

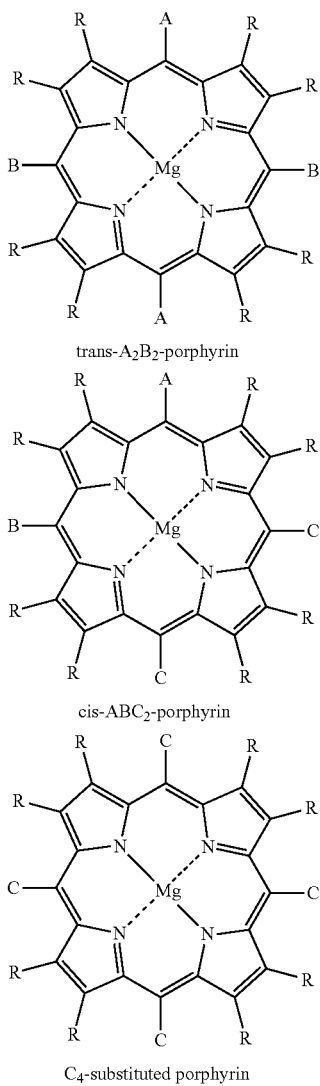

trans-A₂B₂-porphyrin cis-ABC₂-porphyrin

C₄-substituted porphyrin

Again, a chief advantage of the statistical approach is that it provides a straightforward route to cis-substituted and/or sparsely substituted porphyrins, among which include amphipathic architectures containing alkyl and/or heterocyclic groups.

C. Utility

Porphyrin compounds as described herein are useful for a variety of purposes, including but not limited to: as charge storage groups in information storage devices; as detectable groups in a variety of detection techniques; and as chromophores in solar cells, light harvesting rods and light harvesting arrays; as discussed further below.

Information storage devices. Porphyrin compounds described herein are useful immobilized to a substrate for making charge storage molecules and information storage devices containing the same, either individually or as linked polymers thereof, either optionally including additional compounds to add additional oxidation states. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The porphyrins of the invention may comprise a member of a sandwich coordination compound in the information storage molecule, such as described in U.S. Pat. No. 6,212,093 to Li et al. or U.S. Pat. No. 6,451,942 to Li et al.

Detection techniques. Porphyrin compounds as described herein can be detected by any suitable technique and hence used as detectable groups in a variety of techniques, including but not limited to flow cytometry, fluorescence spectroscopy, with a multi-well fluorescent plate scanner, scanning cytometry, fluorescent or immunofluorescent microscopy, laser scanning cytometry, bright field base image analysis, capillary volumetry, manual cell analysis and automated cell analysis. See, e.g., U.S. Pat. Nos. 5,314,805; 6,551,788 and 6,623,982.

Solar cells, light harvesting rods and light harvesting arrays. Porphyrin compounds described herein may be used as chromophores (also referred to as photosensitizers or simply sensitizers) in solar cells, including but not limited to high surface area colloidal semiconductor film solar cells (Gratzel cells), as described in, for example, U.S. Pat. Nos. 5,441,827; 6,420,648; 6,933,436; 6,924,427; 6,913,713; 6,900,382; 6,858,158; and 6,706,963. Compounds described herein may be used as chromophores in the light harvesting rods described in U.S. Pat. Nos. 6,407,330 and 6,420,648 (incorporated herein by reference). The light harvesting rod may comprise one or more porphyrin compound coupled to one or two adjacent chromophores depending upon the position thereof in the light harvesting rod. Such light harvesting rods may be utilized to produce light harvesting arrays as described in U.S. Pat. No. 6,420,648 and solar cells as described in U.S. Pat. No. 6,407,330.

The present invention is explained in greater detail in the following experimental section set forth below, which is to be construed as illustrative and not limiting of the invention.

Experimental

Here we report an efficient, concise, and practical method for preparing magnesium(II)porphine, which greatly facilitates access to this valuable compound, and from which free base porphine is readily obtained.

Results and Discussion

1. Strategy. Our approach for the synthesis of porphine has emerged from our prior studies of routes to trans-substituted porphyrins. The key methods are as follows:

(i) The self-condensation of a dipyrromethane-1-carbinol in the presence of a Lewis acid[19,20] affords the trans-$A_2B_2$ porphyrin. However, the use of this method for the synthesis of porphine suffers from two major drawbacks, low reactivity of hydroxymethyldipyrromethane (1° carbinol) in the acid-catalyzed self-condensation process and lack of an efficient synthetic route to 1-formyldipyrromethane (the most viable precursor for corresponding 1-hydroxymethyldipyrromethane).

(ii) The self-condensation of a 1-acyldipyrromethane in refluxing ethanol containing KOH and a palladium reagent affords the corresponding palladium(II) chelate of a trans-$A_2B_2$-porphyrin.[22]

(iii) The reaction of 1,9-diformyldipyrromethane with n-propylamine and subsequent reaction of the bis(imino)dipyrromethane with a dipyrromethane in the presence of Zn(OAc)₂ in the refluxing ethanol exposed to air affords the zinc(II) complex of the trans-AB-porphyrin.[23] However, application of this method with the unsubstituted dipyrromethane usually resulted in little or no porphyrin.[23]

(iv) As part of our work in chlorin chemistry, we recently developed an efficient route for the synthesis of 1-formyldipyrromethanes.[21] The formylation method entailed traditional Vilsmeier formylation or treatment of a solution of dipyrromethane in THF at room temperature with 2 molar equiv of MesMgBr and then at −78° C. with 2 molar equiv of phenyl formate. The subsequent workup and column chromatography afforded the desired 1-formyldipyrromethane in good yields.

Given the aforementioned developments in porphyrin and dipyrromethane chemistry, and taking into consideration the limitation of existing synthetic methods to porphine in particular and porphyrins in general, we chose 1-formyldipyrromethane 2 as a potentially viable precursor to porphine. The conditions examined are described in the next section.

2. Survey of Approaches. Three approaches for the self-condensation of 2 have been examined (Scheme 1). Each approach should afford direct access to the metalloporphine M-1, thereby sidestepping the difficult purification and handling problems of the poorly soluble free base porphine.[1]

Scheme 1

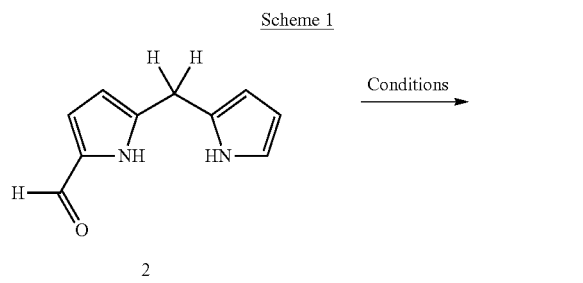

2

Conditions:
(A) Pd(CH$_3$CN)$_2$Cl$_2$, KOH, EtOH, reflux
(B) (i) n-Pr-NH$_2$, (ii) Zn(OAc)$_2$, EtOH, reflux
(C) MgBr$_2$, DBU, toulene, 115° C.

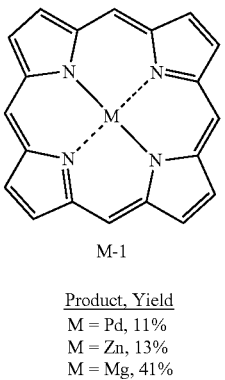

M-1

Product, Yield
M = Pd, 11%
M = Zn, 13%
M = Mg, 41%

A. Formation of Palladium(II)porphine. Reaction of 2 in the presence of a palladium(II) salt under basic conditions in refluxing ethanol [Pd(CH$_3$CN)$_2$Cl$_2$ in EtOH containing KOH][22] afforded palladium(II)porphine (Pd-1) in 11% yield. Palladium(II)porphine was easily purified by filtration through a silica pad.

B. Formation of Zinc(II)porphine. Reaction of 2 with excess n-propylamine in THF at room temperature (conditions used previously with 1,9-diformyldipyrromethanes to form the bis-imine)[23] afforded quantitatively the corresponding imine. The self-condensation of the resulting imine in refluxing EtOH containing Zn(OAc)$_2$ afforded Zn(II)porphine (Zn-1) in 13% yield (yield of isolated porphine determined by absorption spectrometry). Note that due to the symmetrical nature of porphine, any scrambling by the traditional acid-catalyzed pathways is irrelevant.

C. Formation of Magnesium(II)porphine. A lengthy study was carried out to explore the generality of the basic, metal-templated conditions for the self-condensation of 1-acyldipyrromethanes. Such conditions employed Pd(CH$_3$CN)$_2$Cl$_2$ in EtOH containing KOH. The study, which encompassed different metals, solvents, and bases, will be reported elsewhere. One key finding is that a Mg(II) salt (e.g., MgBr$_2$) in the presence of a non-nucleophilic base (e.g., DBU) provides an effective means for the self-condensation of 1-acyldipyrromethanes. The concept leading to the use of MgBr$_2$ and DBU stemmed from our study on the magnesium insertion into porphyrin, wherein similar conditions in the absence of any oxygenic ligands afford the magnesium(II)porphyrin under mild conditions.[24] For the reaction of 2, the formyl group should be activated by coordination to magnesium(II) given the high affinity of magnesium(II) for oxygen. The choice of non-coordinated solvent and non-nucleophilic base is critical to avoid any competition between the solvent and base and the 1-formyldipyrromethane in coordination to magnesium.

Thus, refluxing a mixture of 2 (100 mM) in toluene containing DBU (10 equiv vs. 2) and MgBr$_2$ (3 equiv) in the presence of air afforded Mg(II)porphine (Mg-1) in 41% yield. Note that no quinone oxidant is required. Mg(II)porphine was purified by filtration through an alumina column. No free base porphine was detected in the reaction mixture. The TLC analysis of crude reaction mixture revealed the presence of only Mg-1 and highly polar, polymeric material. Neither starting material nor macrocyclic byproducts were detected. Therefore we performed the purification of Mg-1 without column chromatography. The crude reaction mixture was concentrated. The resulting oily material was treated with THF, filtered (to remove the polymeric material and inorganic salt), and filtrate was concentrated. Subsequent washing with water (to remove an excess of DBU) and crystallization from ethanol/water afforded Mg-1 in satisfactory purity. Mg-1 is stable in solution but undergoes partial decomplexation upon silica column chromatography; fortunately, Mg-1 can be purified by crystallization and no chromatography is required. Note that Mg(II)porphine (Mg-1) was previously prepared by metalation of 1.[2]

The overall stoichiometry for the reaction is shown in Scheme 2. The stoichiometry shows the requirement for a base and an oxidant. The base is required, minimally, to neutralize the two equivalents of HBr liberated upon metal complexation. In this regard, the conditions of MgBr$_2$ and a non-nucleophilic base resemble those for magnesium insertion into free base porphyrins.[24] A 2e−/2H+ oxidant is formally required to form the unsaturated macrocycle. Oxygen present in air would seem a likely source for the oxidizing equivalents. However, the microwave reaction in a degassed flask gave Mg-1 in essentially identical yield to that carried out in an aerobic environment. The essential requirement for both MgBr$_2$ and DBU was validated by omission experiments, where the reaction of 2 carried out in the absence of either DBU or MgBr$_2$ gave no porphine.

Scheme 2

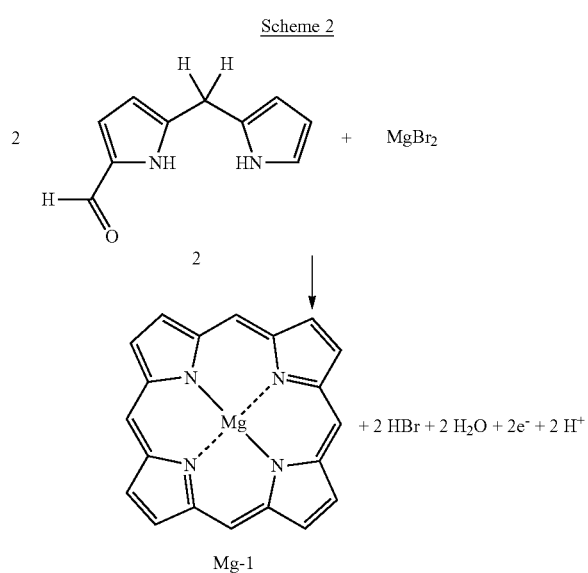

The condensation of 1,9-diformyldipyrromethane with dipyrromethane under analogous conditions afforded Mg-1 albeit in lower yield (18%, Scheme 3).

Scheme 3

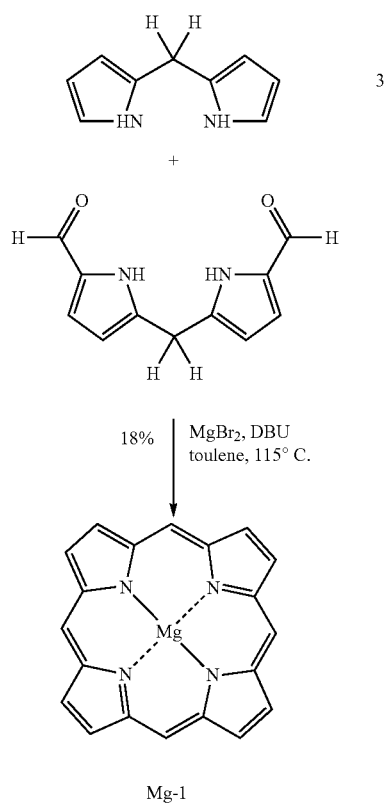

3. Scalable Synthesis of Mg-1. The high yield and the operational simplicity of Mg-1 formation prompted examination of the reaction at multigram scale. Thus, self-condensation of 6.97 g of 2 afforded 2.68 g of Mg-1 in a single batch process. Although the porphine-forming reaction afforded a crude product that could be purified by crystallization (and no chromatography), the synthesis of the precursors required chromatography thereby limiting the scale of reaction.

1-Formyldipyrromethane 2 is the key precursor for the porphine synthesis described herein. Formylation of dipyrromethane via Vilsmeier or Grignard reagent mediated syntheses[21] results in multiple byproducts, requiring tedious chromatographic separation for the purification of 1-formyldipyrromethane (2). The TLC and $^1$H NMR analyses of the crude reaction mixture obtained from Vilsmeier formylation of dipyrromethane showed the presence of three components: starting dipyrromethane (3), 1-formyldipyrromethane (2), 1,9-diformyldipyrromethane (4), and an unknown byproduct (tentatively assigned as a 2-formyldipyrromethane) in a ratio of 7:20:4:1. We were able to separate the desired 2 in 46% yield (without using a tin complexation strategy); however, the purification required lengthy column chromatography.

Given that 2 self-condenses to give Mg-1, and 3+4 undergo reaction to give Mg-1, we decided to examine the porphine-forming reaction with use of the crude mixture derived from Vilsmeier formylation of dipyrromethane (3), which contains 2, 3, and 4. The crude reaction mixture was concentrated under high vacuum to remove DMF (used as a solvent for Vilsmeier formylation). The resulting mixture was dissolved in toluene and treated with DBU and MgBr$_2$ (10 and 3 mol equiv versus dipyrromethane, respectively). The resulting mixture was refluxed until dipyrromethane, 2 and 1,9-diformyldipyrromethane were completely consumed (19 h). The chromatography-free purification as described above afforded Mg-1 in 33% yield (2.21 g). This streamlined, entirely chromatography-free procedure for the synthesis of Mg-1 offers a simple, practical and fast method for preparing multigram quantities of Mg-1 (Scheme 4).

Scheme 4

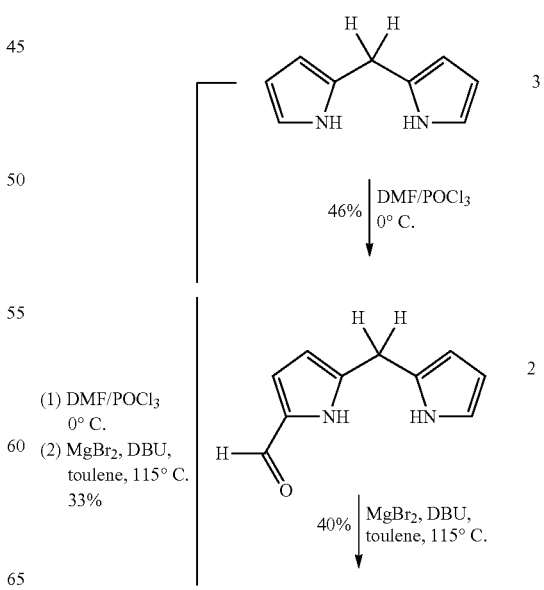

-continued

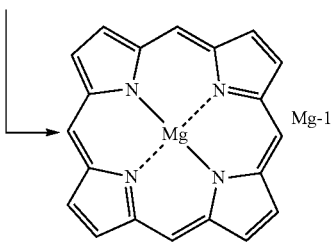

Mg-1

-continued

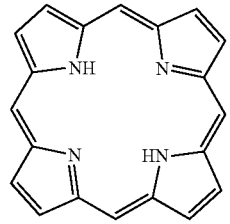

1

We also investigated the synthesis of Mg-1 directly from the crude dipyrromethane (thereby avoiding the purification of any intermediate). The crude reaction mixture containing dipyrromethane (obtained via $InCl_3$-catalyzed reaction of paraformaldehyde with excess pyrrole[26]) was concentrated under high vacuum and subjected to Vilsmeier formylation. The crude product of Vilsmeier formylation was subsequently used for porphine formation. TLC analysis of the crude reaction mixture revealed the presence of Mg-1 and the dipyrromethane. The purification of Mg-1 by crystallization was not successful because of the tarry material in the crude reaction mixture. Therefore this method is less attractive compared to the previously described routes.

4. Solubility. One of the intrinsic problems in porphine chemistry is the poor solubility of 1 in common organic solvents. We compared the solubility of 1, Pd-1, Zn-1 and Mg-1 in common organic solvents ($CH_2Cl_2$, THF, MeOH, ethyl acetate, toluene). The general trend in solubility is as follows: Pd-1<1<Zn-1<<Mg-1. The solubility of Mg-1 in common organic solvents is sufficiently high to perform routine operations (purification, NMR characterization) and perform various reactions at concentrations (1-50 mM) typical of those for porphyrinic compounds.

5. Synthesis of Porphine 1. A streamlined route to free base porphine 1 was examined by demetalation of Mg-1 (Scheme 5). Thus, reaction of 2 in refluxing toluene containing $MgBr_2$ and DBU afforded crude Mg-1. The reaction mixture was concentrated, filtered through an alumina column (to remove excess base and inorganic materials). Treatment of crude Mg-1 with dilute TFA in $CH_2Cl_2$ afforded the free base porphine 1 in 15% overall yield.

Scheme 5

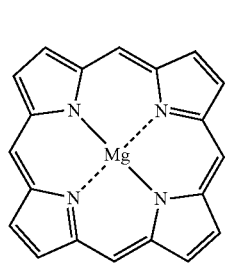

Mg-1

TFA, $CH_2Cl_2$
———————→
15%

Experimental Section

General. $^1H$ NMR spectra (400 MHz) and $^{13}C$ NMR spectra (100 MHz) were collected in $CDCl_3$ at room temperature unless noted otherwise. Silica gel (40 µm average particle size) was used for column chromatography. Anhydrous toluene (Aldrich) was used as received. All other chemicals were reagent grade and were used as received. The 1-formyldipyrromethane 2 is easily detected in TLC upon exposure to $Br_2$ vapor. Grade V alumina was prepared by adding 15 mL of $H_2O$ (Fisher GC grade) to 85 g of alumina (Fisher A-540) with manual stirring.

Noncommercial Compounds. 1-Formyldipyrromethane 2,[21] dipyrromethane 3,[26] and 1,9-diformyldipyrromethane 4[23] were prepared as described in the literature. Zn-1 and Pd-1 were prepared previously via different methods.[25]

Yield Determination. In small-scale reaction, the porphine was purified and isolated by chromatography. Owing to the small quantity of solid porphine, gravimetry was not performed. Instead, the solid sample was dissolved in a known volume of solvent, and the yield was determined by absorption spectrometry, using the molar absorption coefficient of a metalloporphine at the Soret band of 178,800 $M^{-1}$ $cm^{-1}$.[25] This procedure is referred to as the "yield of isolated porphine determined by absorption spectrometry".

Zn(II)porphine (Zn-1). Following a general procedure for porphyrin formation using diformyldipyrromethanes,[23] a sample of 2 (46.0 mg, 0.264 mmol) was treated with n-propylamine (1.00 mL). The resulting mixture was stirred at room temperature for 1 h and then concentrated to afford a brown oil. The resulting imine was dissolved in EtOH (8.6 mL) and treated with $Zn(OAc)_2$ (0.477 g, 2.60 mmol) and refluxed overnight. The reaction mixture was cooled down, and a sample of DDQ (59.0 mg, 0.264 mmol) was added. The resulting mixture was stirred at room temperature for 1 h. The mixture was concentrated and chromatographed (silica, $CH_2Cl_2$) to obtain a purple solid (13%, yield of isolated porphine determined by absorption spectrometry): $^1H$ NMR (THF-$d_8$) δ 9.55 (s, 8H), 10.34 (s, 4H); LD-MS obsd 372.0; FAB-MS obsd 372.0342, calcd 372.0353 ($C_{20}H_{12}N_4Zn$); $\lambda_{abs}$ 399, 526 nm.

Pd(II)porphine (Pd-1). Following a general procedure for porphyrin formation using 1-acyldipyrromethanes,[22] a sample of 2 (0.172 g, 1.00 mmol), KOH (0.280 g, 5.00 mmol) and $Pd(CH_3CN)_2Cl_2$ (0.155 g, 0.600 mmol) was treated with EtOH (10 mL). The resulting suspension was stirred at room temperature for 1 min and then refluxed for 1 h. The reaction mixture was concentrated and chromatographed (silica, $CH_2Cl_2$) to obtain a pink-orange solid (22 mg, 11%): $^1H$ NMR δ 9.46 (s, 8H), 10.38 (s, 4H); LD-MS obsd 414.2; calcd 414.0097 ($C_{20}H_{12}N_4Pd$); $\lambda_{abs}$ 393, 503, 536 nm.

Mg(II)porphine (Mg-1). A suspension of 2 (0.174 g, 1.00 mmol) in toluene (10 mL) was treated dropwise with DBU (1.49 mL, 10.0 mmol). The resulting solution was stirred at room temperature for 5 min and treated with a sample of MgBr$_2$ (0.552 g, 3.00 mmol). The resulting suspension was placed in oil bath (preheated to 135° C.) and stirred at 135° C. open to the air for 14 h. The reaction mixture was concentrated under vacuum, dissolved in CH$_2$Cl$_2$ and filtered through an alumina column [CH$_2$Cl$_2$/ethyl acetate (4:1)→ethyl acetate→CH$_2$Cl$_2$/MeOH (5:1)]. Fractions containing Mg-1 were collected and concentrated. The resulting oily residue was dissolved in CH$_2$Cl$_2$. The organic solution was washed with water and brine, dried (K$_2$CO$_3$), concentrated and filtered through alumina grade V (CH$_2$Cl$_2$) to afford a purple solid (67 mg, 41%): $^1$H NMR (THF-d$_8$) δ 9.47 (s, 8H), 10.26 (s, 4H); $^{13}$C NMR δ 104.8, 131.6, 149.0; LD-MS obsd 331.7; FAB-MS obsd 332.0929, calcd 332.0912 (C$_{20}$H$_{12}$N$_4$Mg); λ$_{abs}$ 402, 536 nm.

Porphine (1). A sample of DBU (6.91 mL, 46.2 mmol, 10.0 mol equiv versus 2) was added dropwise to a suspension of 2 (0.805 g, 4.62 mmol, 100 mM) in toluene (46 mL). MgBr$_2$ (2.55 g, 13.9 mmol, 3.00 mol equiv) was added to the reaction mixture in a single portion. The reaction mixture was heated to 115° C. (preheated oil bath temperature 115° C.) with exposure to air for 6 h. TLC analysis (silica, CH$_2$Cl$_2$/ethyl acetate 1:3) revealed only a trace amount of starting material. A 1-μL aliquot was removed from the reaction mixture and examined by absorption spectroscopy (CH$_2$Cl$_2$). Four peaks were observed (302, 383, 403 and 526 nm). The crude reaction mixture was concentrated and chromatographed [alumina grade V, 500 g, 4 cm dia×35 cm, loaded with CH$_2$Cl$_2$ and eluted with CH$_2$Cl$_2$/ethyl acetate (4:1→1:1)] afforded a purple solid. The concentrated fraction was checked by $^1$H NMR spectroscopy whereupon ~10% starting material was observed. The concentrated product was dissolved in a minimum amount of CH$_2$Cl$_2$ (~2 mL). The solution was treated with hexanes (~15 mL) to afford a precipitate. The mixture was centrifuged. The collected precipitate was dried under high vacuum and checked by $^1$H NMR spectroscopy. Less than 5% starting material was observed. The product was dissolved in CH$_2$Cl$_2$ (93 mL), and TFA (2.15 mL) was added. The reaction mixture was stirred vigorously at room temperature for 1 h. The crude reaction mixture was checked by absorption spectroscopy and TLC analysis (silica, CH$_2$Cl$_2$). No Mg(II)porphine was observed. The reaction mixture was neutralized by addition of saturated aqueous NaHCO$_3$. The organic layer was washed (water and brine), dried (Na$_2$SO$_4$), concentrated, and chromatographed [silica, 200 g, 2 cm dia× 30 cm] to afford a purple solid (0.106 g, 15%): $^1$H NMR (DMF-d$_7$) δ (−3.98)-(−3.96) (brs, 2H), 9.80 (s, 8H), 10.69 (s, 4H); $^{13}$C NMR (DMF-d$_7$) δ 104.5, 132.2-432.3 (brs); LD-MS obsd 309.7; λ$_{abs}$ 396, 490, 564 nm.

Protocol A: Large-scale Synthesis of Mg-1 Directly from 1-Formyldipyrromethane at 100 mM. A sample of 1-formyldipyrromethane 2 (6.97 g, 40.0 mmol) was placed in a 1000 mL oven-dried round bottom flask. A teflon septum was attached and toluene (400 mL) was added via cannula. The reaction mixture was heated to 80° C., whereupon DBU (60 mL, 400 mmol, 10 mol equiv versus 2) was added dropwise under vigorous stirring in 10 min. The resulting mixture was stirred for 5 min (the temperature of the reaction mixture increased from 80° C. to 98° C.). The mixture darkened. The septum was removed and MgBr$_2$ (22.1 g, 120 mmol, 3.0 mol equiv versus 2) was added in one portion under vigorous stirring (Note 1). The reaction flask was attached to the reflux condenser, and heated at 115° C. with exposure to air. On the basis of TLC analysis (silica, CH$_2$Cl$_2$/ethyl acetate 5:1) and absorption spectroscopy, porphyrin formation was complete in 19 h. The crude reaction mixture was concentrated. The resulting residue was treated with THF (400 mL) and stirred vigorously 20 min at room temperature. The reaction mixture was filtered through a Buchner funnel. The filtrate was concentrated (fraction A). The filter cake was mixed with THF (200 mL) and heated to reflux for 1 h (Note 2). The resulting mixture was filtered through a Bucher funnel, and the filter cake was washed with THF (10×10 mL). The collected filtrate was concentrated and combined with fraction A. The resulting crude product was combined with ethyl ether (400 mL), washed [water (200 mL), brine (5×200 mL)] and concentrated (Note 3). The crude product was purified by crystallization (ethanol/water 1:4). Porphine Mg-1 was obtained as a purple solid (2.68 g, 40%).

Note 1: A dry flask is essential, as is vigorous stirring, so that MgBr$_2$ does not reside as a solid on the bottom of the flask, which typically lowers the yield of porphyrin formation.

Note 2: After the first filtration, some of the magnesium porphine stayed with the filter cake. The cake needs to be heated in THF at reflux to dissolve any remaining porphine.

Note 3: Excess DBU makes the aqueous work-up difficult. A trace amount of MeOH and Na$_2$SO$_4$ was used to facilitate phase separation.

Vilsmeier Formylation of Dipyrromethane (3) Affording 1-Formyldipyrromethane 2. A sample of DMF (30 mL) was treated with POCl$_3$ (4.5 mL, 49.2 mmol) at 0° C. under argon, and the resulting solution was stirred for 10 min (Vilsmeier reagent). A solution of 3 (5.84 g, 40.0 mmol) in DMF (120 mL) at 0° C. under argon was treated with the freshly prepared Vilsmeier reagent (25 mL, 41 mmol), and the resulting solution was allowed to stir for 1.5 h at 0° C. The reaction mixture was poured into a mixture of 2 M NaOH (300 mL) and CH$_2$Cl$_2$ (200 mL) at 0° C. A blue color was observed. The reaction mixture was stirred for 20 min at 0° C. The reaction mixture turned to orange brown. The organic phase was extracted with CH$_2$Cl$_2$. The collected organic phase was washed with NH$_4$Cl (200 mL). The organic phase was separated, washed with water and brine, and dried (NaSO$_4$). The collected organic phase was concentrated to give a red, oily crude product. The remaining DMF was removed under high vacuum (1 h, 50° C.), resulting in a light pink solid material. The crude product was purified by column chromatography (silica, CH$_2$Cl$_2$→CH$_2$Cl$_2$/ethyl acetate 5:1) to give a yellow solid (3.198 g, 46%). The data ($^1$H NMR, mp, elemental analysis) were consistent with those obtained from samples prepared via earlier routes.

Synthesis of Mg-1 Directly from Crude 1-Formyldipyrromethane at 100 mM. Vilsmeier formylation of 3 (5.84 g, 40.0 mmol) was performed following the above procedure. The resulting crude pink solid was used for the porphine synthesis without purification. By following Protocol A, the crude product was dissolved in toluene (400 mL). A sample of DBU (60 mL, 400 mmol, 10 mol equiv versus 3) and MgBr$_2$ (22.1 g, 120 mmol, 3 mol, equiv versus 3) were added. Crystallization of the resulting crude product afforded Mg-1 as a purple solid (2.21 g, 33%). The data ($^1$H NMR, $^{13}$C NMR, absorption spectrum and FAB-MS) were consistent with those obtained from samples prepared via earlier routes.

Synthesis of Mg-1 from 2 at 100 mM. By following Protocol A, a sample of 2 (6.97 g, 40.0 mmol) was dissolved in toluene (400 mL). Samples of DBU (60 mL, 400 mmol, 10 mol equiv versus 2) and MgBr$_2$ (22.1 g, 120 mmol, 3 mol, equiv versus 2) were added. Crystallization of the resulting crude product afforded Mg-1 as a purple solid (2.681 g, 40%). The data ($^1$H NMR, $^{13}$C NMR, absorption spectrum and FAB-MS) were consistent with those obtained from samples prepared via earlier routes.

Synthesis of Mg-1 via 1,9-Diformyldipyrromethane. By following the general procedure, a sample of DBU (0.750 mL, 5.00 mmol) was added dropwise to a suspension of 3 (36 mg, 0.25 mmol) and 4 (50 mg, 0.25 mmol) in toluene (5 mL). MgBr$_2$ (276 mg, 1.5 mmol, 3.00 mol equiv) was added to the reaction mixture in a single portion. The reaction mixture was heated to 115° C. (preheated oil bath temperature 115° C.) with exposure to air for 36 h. Column chromatography (alumina, grade V, CH$_2$Cl$_2$) afforded Mg-1 in 18% yield.

TABLE 1

Reported Methods for Porphine Synthesis.

| Entry | Starting material | Conditions | Isolated product (mg) | Yield (%) | Ref. |
|---|---|---|---|---|---|
| 1 | 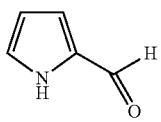 | HCOOH, reflux | 17 | 0.1 | 6 |
| 2 |  + CH$_2$O | propionic acid, pyridine 95° C. pyridine/MeOH sealed tube | 130 ~3 | 0.9 ~0.02 | 8 7 |
| 3 |  | Ethylbenzene 100° C., 11.5 days | NR$^a$ | 18.02 | 10 |
| | | (1) 4-methyl-2-pentanone/AcOH/H$_2$O (2) DDQ | 30 | 15.3 | 12 |
| | | DMF, pH = 3.7 145° C. various metal salt | Up to 200 | Up to 20.3$^b$ | 11 |
| | | H$_2$O/AcOH Mg(OAc)$_2$ (0.2%) potassium persulfate | 0.3 | 5.33 | 9 |
| | | (1) HCl, H$_2$O/SDS$^c$ (2) DDQ | 2 | 2 | 13 |
| 4 | 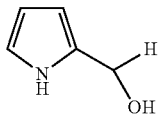 | (1) EtMgBr, chlorobenzene 180° C. (2) Cu(OAc)$_2$, AcOH | 12 | 3.86 | 14 |
| 5 | 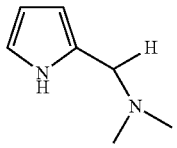 + 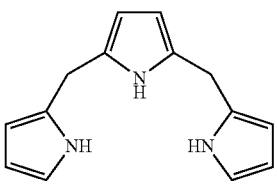 | (1) BF$_3$·MeOH (2) p-chloranil | NR | 31$^c$ | 18 |
| 6 | 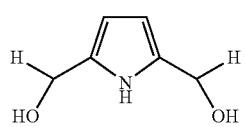 | H$_2$SO$_4$/1-butanol 90° C., 15 min | 86 | 74 | 16 |

TABLE 1-continued

Reported Methods for Porphine Synthesis.

| Entry | Starting material | Conditions | Isolated product (mg) | Yield (%) | Ref. |
|---|---|---|---|---|---|
| 7 | (structure) | $H_2SO_4$ 200° C., 15 min | 74 | 64 | 17 |

[a] Not reported.
[b] This yield is claimed to be non-reproducible; see reference 12.
[c] SDS - sodium dodecyl sulfate.
[d] Yield was determined by absorption spectroscopy.

REFERENCES (1) Nudy, L. R.; Coffey, J. C.; Longo, F. R. *J. Heterocyclic Chem.* 1982, 19, 1589-1560.
(2) Shi, D.-F.; Wheelhouse, R. T. *Tetrahedron Lett.* 2002, 43, 9341-9342.
(3) Schlozer, R.; Fuhrhop, J.-H. *Angew. Chem. Int. Ed.* 1975, 14, 363-363.
(4) Hatscher, S.; Senge, M. O. *Tetrahedron Lett.* 2003, 44, 157-160
(5) Neya, S.; Funasaki, N. *J. Biol. Chem.* 1993, 268, 8935-8942.
(6) Fischer, H.; Gleim, W. *Liebigs Ann.* 1936, 521, 157-160.
(7) Rothemund, P. *J. Am. Chem. Soc.* 1935, 57, 2010-2011. (b) Rothemund, P. *J. Am. Chem. Soc.* 1936, 57, 625-627.
(8) Neya, S.; Yodo, H.; Funasaki, N. *J. Heterocyclic Chem.* 1993, 30, 549-550.
(9) Krol, S. *J. Org. Chem.* 1959, 24, 2065-2067.
(10) Longo, F. R.; Thorne, E. J.; Adler, A. D.; Dym, S. *J. Heterocyclic Chem.* 1975, 12, 1305-1309.
(11) Yalman, R. G. U.S. Pat. No. 3,579,533.
(12) Ellis, P. E.; Langdale, W. A. *J. Porphyrins Phthalocyanines* 1997, 1, 305-307.
(13) Bonar-Law, R. P. *J. Org. Chem.* 1996, 61, 3623-3634.
(14) Eisner, U.; Linstead, R. P. *J. Chem. Soc.* 1955, 3742-3749.
(15) Egorova, G. D.; Solov'ev, K. N.; Shul'ga, A. M. *J. Gen. Chem.* (*USSR*) 1967, 37, 333-336.
(16) Neya, S.; Quan, J.; Hoshino, T.; Hata, M.; Funasaki, N. *Tetrahedron Lett.* 2004, 45, 8629-8630.
(17) Neya, S.; Funasaki, N. *Tetrahedron Lett.* 2002, 43, 1057-1058.
(18) Taniguchi, S.; Hasegawa, H.; Nishimura, M.; Takahashi, M. *Synlett* 1999, 73-74.
(19) Rao, P. D.; Littler, B. J.; Geier, G. R., III; Lindsey, J. S. *J. Org. Chem.* 2000, 65, 1084-1092.
(20) Zaidi, S. H. H.; Fico, R. M., Jr.; Lindsey, J. S. *Org. Process Res. Dev.* 2006, 10, 118-134.
(21) Ptaszek, M.; McDowell, B. E.; Lindsey, J. S. *J. Org. Chem.* 2006, 71, 4328-4331.
(22) Sharada, D. S.; Muresan, A. Z.; Muthukumaran, K.; Lindsey, J. S. *J. Org. Chem.* 2005, 70, 3500-3510.
(23) Taniguchi, M.; Balakumar, A.; Fan, D.; McDowell, B. E.; Lindsey, J. S. *J. Porphyrins Phthalocyanines* 2005, 9, 554-574
(24) Woodford, J. N.; Lindsey, J. S. *Inorg. Chem.* 1995, 34, 1063-1069.
(25) Barth, G.; Linder, R. E.; Waespe-Sarcevic, N.; Bunnenberg, E.; Djerassi, C.; Aronowitz, Y. J.; Gouterman, M. *J. Chem. Soc. Perkin Trans.* 2 1977, 337-343.
(26) Laha, J. K.; Dhanalekshmi, S.; Taniguchi, M.; Ambroise, A.; Lindsey, J. S. *Org. Process Res. Dev.* 2003, 7, 799-812.

The foregoing is illustrative of the present invention, and is not to be construed as limiting thereof. The invention is defined by the following claims, with equivalents of the claims to be included therein.

That which is claimed is:

1. A method of making porphine, comprising:
   condensing (a) (i) 1-formyl dipyrromethane with itself, (ii), condensing 1,9-diformyldipyrromethane with dipyrromethane, or (iii) concurrently both condensing 1-formyl dipyrromethane with itself while also condensing 1,9-diformyldipyrromethane with dipyrromethane, with (b) a metal salt under basic conditions to produce said porphine;
   wherein said metal salt is a magnesium, zinc, nickel or indium salt.

2. The method of claim 1, wherein said condensing comprises condensing 1-formyl dipyrromethane with itself.

3. The method of claim 1, wherein said condensing comprises condensing 1,9-diformyldipyrromethane with dipyrromethane.

4. The method of claim 1, wherein said condensing comprises concurrently condensing 1-formyl dipyrromethane with itself while also condensing 1,9-diformyldipyrromethane with dipyrromethane.

5. The method of claim 1, wherein said metal salt is a magnesium or zinc salt.

6. The method of claim 1, wherein said metal salt is a magnesium halide.

7. The method of claim 1, further comprising the step of displacing said metal to form free base porphine.

8. The method of claim 1, wherein said self-condensing step is carried out by microwave irradiation.

9. The method of claim 1, wherein said self-condensing step is carried out in a non-coordinating or weakly coordinating solvent.

10. The method of claim 1, wherein said self-condensing step is carried out in a non-coordinating or weakly coordinating solvent in the presence of a non-coordinating or weakly coordinating base.

* * * * *

UNITED STATES PATENT AND TRADEMARK OFFICE
CERTIFICATE OF CORRECTION

PATENT NO. : 7,964,720 B2
APPLICATION NO. : 12/960057
DATED : June 21, 2011
INVENTOR(S) : Kiper et al.

It is certified that error appears in the above-identified patent and that said Letters Patent is hereby corrected as shown below:

Column 8, Line 52: correct "cycloalkylalky S(O)$_m$"
to read -- cycloalkylalky—S(O)$_m$ --

Column 21, Scheme 3, first figure: correct

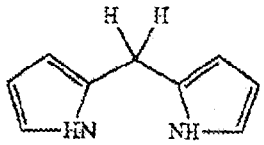

to read

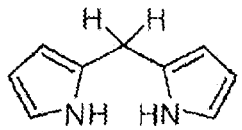

Signed and Sealed this
Twenty-ninth Day of November, 2011

David J. Kappos
*Director of the United States Patent and Trademark Office*